United States Patent
Kobayashi

(10) Patent No.: US 10,304,218 B2
(45) Date of Patent: May 28, 2019

(54) IMAGE RECONSTRUCTION PROCESSING METHOD

(71) Applicant: SHIMADZU CORPORATION, Kyoto (JP)

(72) Inventor: Tetsuya Kobayashi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 200 days.

(21) Appl. No.: 15/320,244

(22) PCT Filed: Jul. 4, 2014

(86) PCT No.: PCT/JP2014/067976
§ 371 (c)(1),
(2) Date: Dec. 19, 2016

(87) PCT Pub. No.: WO2016/002084
PCT Pub. Date: Jan. 7, 2016

(65) Prior Publication Data
US 2017/0154444 A1    Jun. 1, 2017

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/037* (2013.01); *A61B 6/4266* (2013.01);
(Continued)

(58) Field of Classification Search
CPC .... G01S 15/8977; G06T 11/00; G06T 11/003; G06T 11/005; G06T 11/006; G06T 11/008
See application file for complete search history.

(56) References Cited

U.S. PATENT DOCUMENTS

2003/0128877 A1* 7/2003 Nicponski ......... G06K 9/00221
382/224
2007/0121779 A1* 5/2007 Nishide ............... G06T 11/005
378/4
(Continued)

FOREIGN PATENT DOCUMENTS

| JP | 61-225640 A | 10/1986 |
|---|---|---|
| JP | 2008-245695 A | 10/2008 |
| JP | 4660706 B2 | 3/2011 |

OTHER PUBLICATIONS

Shepp, L. A. et al., "Maximum Likelihood Reconstruction for Emission Tomography," IEEE Transactions on Medical Imaging, vol. MI-1, No. 2, Oct. 1982, pp. 113-122.
(Continued)

*Primary Examiner* — Solomon G Bezuayehu
(74) *Attorney, Agent, or Firm* — McDermott Will & Emery LLP

(57) ABSTRACT

An image reconstruction processing method according to this invention is characterized by adding weight to conventional reconstruction processing steps. That is, weighting is performed when performing the reconstruction process based on optimization calculations of a multivariate function in which a digital image is unknown, and which consists of data function generalized from the likelihood function of Poisson distribution. When a weight coefficient is a constant independent of element data, for example, the weight coefficient is set based on directionality of linear noises occurring in a reconstruction image, or the weight coefficient is set based on detection depth position information of detector elements of DOI detectors (step S1). By weighting partial functions with weight coefficients of back projection to a reconstruction image of the element data corresponding to the partial functions, artifacts appearing on the image can be suppressed, or the spatial resolution of the image can be improved.

9 Claims, 5 Drawing Sheets

(51) Int. Cl.
    *A61B 6/03*     (2006.01)
    *A61B 6/00*     (2006.01)
    *G01T 1/172*     (2006.01)
    *G01T 1/29*     (2006.01)
    *G06T 7/00*     (2017.01)

(52) U.S. Cl.
    CPC ............ *A61B 6/502* (2013.01); *A61B 6/5258* (2013.01); *G01T 1/172* (2013.01); *G01T 1/2985* (2013.01); *G06T 7/0012* (2013.01); *G06T 11/006* (2013.01); *G06T 2207/10081* (2013.01); *G06T 2207/10104* (2013.01); *G06T 2207/10108* (2013.01)

(56) References Cited

U.S. PATENT DOCUMENTS

| | | | | |
|---|---|---|---|---|
| 2009/0279768 A1* | 11/2009 | Nishikawa | ............ | A61B 6/032 382/132 |
| 2010/0032574 A1 | 2/2010 | Yoshida et al. | | |
| 2010/0046818 A1 | 2/2010 | Yamaya et al. | | |
| 2010/0215140 A1* | 8/2010 | Sauer | ...................... | A61B 6/032 378/4 |
| 2011/0299792 A1* | 12/2011 | Sakaguchi | .............. | G06T 11/00 382/255 |
| 2012/0250968 A1* | 10/2012 | Kappler | ................. | A61B 6/032 382/131 |
| 2013/0177132 A1* | 7/2013 | Takahashi | ............. | G06T 11/006 378/4 |
| 2013/0294568 A1* | 11/2013 | Lee | ........................... | G06T 5/50 378/4 |
| 2015/0164456 A1* | 6/2015 | Takamatsu | .............. | A61B 6/482 378/4 |

OTHER PUBLICATIONS

International Search Report dated Oct. 7, 2014, issued in PCT/JP2014/067976, with English language translation.

* cited by examiner (a)

(b)

IMAGE RECONSTRUCTION PROCESSING METHOD

CROSS REFERENCE

This application is a U.S. National Stage application under 35 U.S.C. § 371, of International Application PCT/JP2014/067976 filed on Jul. 4, 2014, which was published as WO 2016/002084 on Jan. 7, 2016. The application is incorporated herein by reference.

TECHNICAL FIELD

This invention relates to an image reconstruction processing method for performing a reconstruction process for reconstructing, from a measurement data set of a subject obtained by a radiation detecting apparatus, a physical quantity distribution of the subject relating to an occurrence factor of the measurement data set, as a multidimensional digital image.

BACKGROUND ART

This image reconstruction processing method is used in the whole image reconstruction technique of tomographic imaging apparatus (CT (Computed Tomography) apparatus) with radiation detecting apparatus. The tomographic imaging apparatus with the radiation detecting apparatus include, for example, nuclear medicine diagnostic apparatus and X-ray computerized tomographic apparatus (X-ray CT apparatus). The reconstruction process is performed for reconstructing, from a measurement data set of a subject obtained by the radiation detecting apparatus, a physical quantity distribution of the subject relating to an occurrence factor of the measurement data set as a multidimensional digital image (such as a sectional image or a 3D reconstruction image).

The nuclear medicine diagnostic apparatus include a positron emission tomographic apparatus (PET (Positron Emission Tomography) apparatus) and a single photon emission tomographic apparatus (SPECT (Single Photon Emission CT) apparatus). The PET apparatus detects a plurality of radioactive rays (gamma rays) generated by annihilation of positrons, records detection signals only when a plurality of detectors detect the radioactive rays (gamma rays) simultaneously (that is, only when coincidences are counted), and performs a reconstruction process on the detection signals (numerous gamma ray detection signals) to create tomographic images of the subject. The SPECT apparatus detects a single radioactive ray (gamma ray), and performs a reconstruction process to create tomographic images of the subject.

To describe this by taking for example the nuclear medicine diagnostic apparatus (emission CT apparatus) such as the PET apparatus and SPECT apparatus, a reconstruction processing technique (ML reconstruction method) for an emission CT image based on maximum likelihood (ML: Maximum Likelihood) of Poisson distribution has been proposed in the field of emission CT apparatus (see Nonpatent Document 1, for example). In the image reconstruction technique used with the PET apparatus and SPECT apparatus today, although different from one apparatus maker to another, the mathematical framework (theory serving as a foundation) of almost all techniques is the ML reconstruction method described in Nonpatent Document 1. In this sense, in the field of emission CT apparatus, Nonpatent Document 1 is a very famous treatise about the ML reconstruction method. Almost all of today's image reconstruction methods can be said analogs of the technique described in Nonpatent Document 1.

A measurement data set (that is, measurement data) of a subject obtained by a radiation detecting apparatus includes statistical errors, and a distribution of statistical errors (error distribution) follows Poisson distribution. The ML reconstruction method described in Nonpatent Document 1 is a method for obtaining as a likely radioactivity distribution image (physical quantity distribution) a solution (image) which maximizes a likelihood function derived from Poisson characteristics of measurement data. When an extension is made to an error distribution (e.g. Gaussian distribution) other than Poisson distribution, as in the field of X-ray CT apparatus, the likelihood function is generally also called "data function". The maximization of the likelihood function is performed using a repeated calculation algorithm (iterative method).

When the likelihood function of Poisson distribution is represented by L(x), the likelihood function L(x) of Poisson distribution is expressed by the following equation (1):

[Math 1]

$$L(x) = \sum_{i=1}^{I} a_i \cdot x - \sum_{i=1}^{I} y_i \log(a_i \cdot x + r_i) \quad (1)$$

Here, x is a reconstructed image vector (however, pixel values are non-negative), I is the number of measurement data points, $a_i$ is a sensitivity distribution function at an i-th measurement data point (an i-th row vector of system matrix A), $y_i$ is a prompt coincidence value (count value) at the i-th measurement data point, and $r_i$ is estimated values of count values of coincidences (random coincidences and scatter coincidences) other than the prompt coincidence value (count value) at the i-th measurement data point.

PRIOR ART DOCUMENT

Nonpatent Document

[Nonpatent Document 1]
L. A. Shepp and Y. Vardi. Maximum likelihood reconstruction for emission tomography. IEEE Trans. Med. Imaging, Vol. 1, pp. 113-122, 1982.

SUMMARY OF INVENTION

Technical Problem

The image reconstruction method (ML reconstruction method) described in Nonpatent Document 1 and image reconstruction methods derived from this technique have been established as mathematical theories. However, when these methods are directly applied to actual measured data, the following problems may arise:

(i) Streak artifacts which are linear noises appear in the image, and (ii) The spatial resolution of the image is lower than a value predicted from apparatus parameters (mainly a size of radiation detector elements). Although these are issues (problems) occurring in nuclear medicine diagnostic apparatus (emission CT apparatus), it is thought that artifacts and deterioration of spatial resolution of the image occur also when an extension is made to X-ray computerized tomographic apparatus (X-ray CT apparatus).

This invention has been made having regard to the state of the art noted above, and its object is to provide an image reconstruction processing method which can suppress artifacts appearing in images and improve the spatial resolution of images.

Solution to Problem

To fulfill the above object, this invention provides the following construction.

An image reconstruction processing method according to this invention is an image reconstruction processing method for performing an image reconstruction process to reconstruct as a multidimensional digital image, from a measurement data set of a subject obtained by a radiation detecting apparatus, a physical quantity distribution of the subject relating to an occurrence factor of the measurement data set, wherein a first multivariate function in which the digital image is regarded as unknown is (1) a data function expressed by a sum of partial functions composed based on an error distribution of element data constituting the measurement data set; or (2) a sum of the data function expressed by the sum of the partial functions composed based on the error distribution of the element data constituting the measurement data set, and a second multivariate function composed based on prior information on the physical quantity distribution; and the image reconstruction processing method weights the partial functions with a weight coefficient of back projection of a reconstruction image of the element data corresponding to the partial functions, and executes reconstruction processing steps based on optimization calculations of the multivariate function consisting of the weighted data function or the sum of the weighted data function and the second multivariate function composed based on prior information on the physical quantity distribution.

The image reconstruction processing method according to this invention is characterized by adding weight to the conventional reconstruction processing steps. That is, weighting is performed when performing the reconstruction process based on optimization calculations of a multivariate function in which a digital image is unknown, and which consists of a data function generalized from the likelihood function of the Poisson distribution in Nonpatent Document 1. Assuming here that the multivariate function in which the digital image is unknown is the "first multivariate function", the first multivariate function is expressed in (1) or (2) below. Thus, the first multivariate function is (1) a data function expressed by a sum of partial functions composed based on an error distribution of element data constituting a measurement data set (of a subject obtained by the radiation detecting apparatus). Or the multivariate function is (2) a sum of the data function stated in (1) and a multivariate function composed based on prior information on the physical quantity distribution (of the subject relating to an occurrence factor of the measurement data set) (the multivariate function composed based on prior information on the physical quantity distribution will be called hereinafter the "second multivariate function" to distinguish from the first multivariate function.) And the partial functions are weighted with weight coefficients of back projection to the reconstruction image of the element data corresponding to the partial functions noted above. These weight coefficients are non-negative coefficients (also called "influence adjusting coefficients") which adjust the influence rates of the element data on the reconstruction image. By weighting the partial functions with these weight coefficients, artifacts appearing on the image can be suppressed, or the spatial resolution of the image can be improved.

In the image reconstruction processing method according to this invention, the radiation detecting apparatus is one of a positron emission tomographic apparatus (PET apparatus), a single photon emission tomographic apparatus (SPECT apparatus), and an X-ray computerized tomographic apparatus (X-ray CT apparatus).

When the radiation detecting apparatus is either a PET apparatus, a SPECT apparatus or an X-ray CT apparatus, and when the above-noted linear noises (streak artifacts) occur, it is thought due to the reconstruction process being performed using the partial functions without setting weight coefficients, as in conventional practice. So, the linear noises (streak artifacts) can be suppressed by setting a weight coefficient based on the directionality of the linear noises appearing on the reconstruction image when the weight coefficient is a constant independent of the element data.

More particularly, the weight coefficient (weight coefficient larger than 0, however) for the element data along the running direction of the linear noises is set to a value smaller than the weight coefficient (weight coefficient larger than 0) for the element data not along the running direction of the linear noises. This relatively lessens the influence of the measurement data set along the linear noises (streak artifacts). As a result, the linear noises (streak artifacts) can be suppressed.

The above linear noises (streak artifacts) occur more easily when detector units constructed to have opened space are used than full ring type detector units. In the case of the detector units constructed to have opened space, radiation passing through the opened space (omission portion) is not detected. Therefore, the partial loss of projection data causes noise having strong spatial correlation on the reconstruction image. Particularly when a plurality of detector units separated from each other are used, the linear noises (streak artifacts) are thought to occur along straight line directions connecting between detector elements in the same detector unit.

Then, the viewpoint is changed, and when the radiation detectors constituting the radiation detecting apparatus are constructed of a plurality of detector units separated from each other, the weight coefficient (weight coefficient larger than 0, however) for the element data along the straight line directions connecting between detector elements in the same detector unit is set to a value smaller than the weight coefficient (weight coefficient larger than 0) for the element data along the straight line directions connecting between the detector elements in the mutually different detector units. This can suppress the linear noises (streak artifacts) appearing along the straight line directions connecting between the detector elements in the same detector unit.

In the case of a nuclear medicine diagnostic apparatus (emission CT equipment) except an X-ray CT apparatus, the radiation detecting apparatus is one of a positron emission tomographic apparatus (PET apparatus) and a single photon emission tomographic apparatus (SPECT apparatus). When the nuclear medicine diagnostic apparatus is either a PET apparatus or a SPECT apparatus, the above measurement data set (of the subject obtained by the radiation detecting apparatus) is one of sinogram data, histogram data, and list mode data.

When the nuclear medicine diagnostic apparatus is either a PET apparatus or a SPECT apparatus, and the measurement data set is either sinogram data, histogram data or list mode data, and when deterioration occurs in the spatial resolution of the above-noted image, it is thought due to the reconstruction process being performed using partial functions without setting weight coefficients, as in conventional practice. Particularly when the radiation detectors constituting the radiation detecting apparatus are constructed to measure detection depth position information on radiation, that is, when DOI detectors are used which are constructed by stacking each detecting element in the depth direction of radiation, the following phenomenon happens. That is, of a detecting element pair close to the object of measurement (shallow DOI layer) and a faraway detecting element pair (deep DOI layer), the latter has the larger range of sensitivity distribution function, and hence the latter has a lower degree of reliability than the former. So, the spatial resolution of image can be improved by setting weight coefficients depending on the detection depth position information corresponding to the measurement data set.

More particularly, when N is a natural number larger than or equal to 2, the radiation detectors are constructed to measure detection depth position information of N stages (that is, constructed of DOI detectors). In the detector elements constituting the radiation detectors, stage numbers of detection depth of two detector elements having measured a coincidence are set to g and h ($1 \leq g$, $h \leq N$), respectively, so that the numbers become larger from shallow stage to deep stage. At this time, the weight coefficient is a two-dimensional function having the stage numbers g and h as discrete variables, the two-dimensional function being such that a one-dimensional function for the other variable obtained when one variable is fixed is a nonincreasing function. Consequently, the spatial resolution of the image can be improved by weighting in which count data measured by pairs in deep DOI layers having a low degree of reliability is multiplied by a smaller weight coefficient than count data measured by pairs in shallow DOI layers having a high degree of reliability.

In the image reconstruction processing method according to these inventions, the error distribution is one of Poisson distribution and Gaussian distribution. The error distribution, when it is Poisson distribution, is used with a nuclear medicine diagnostic apparatus (emission CT apparatus). The error distribution, when it is Gaussian distribution, is used with an X-ray computerized tomographic apparatus (X-ray CT apparatus).

Advantageous Effects of Invention

The image reconstruction processing method according to this invention performs weighting when performing a reconstruction process based on optimization calculations of a multivariate function in which a digital image is unknown, and which consists of a data function, for example. By weighting partial functions with weight coefficients of back projection to a reconstruction image of element data corresponding to the partial functions, artifacts appearing on the image can be suppressed, or the spatial resolution of the image can be improved.

EMBODIMENT 1

Figure 1:
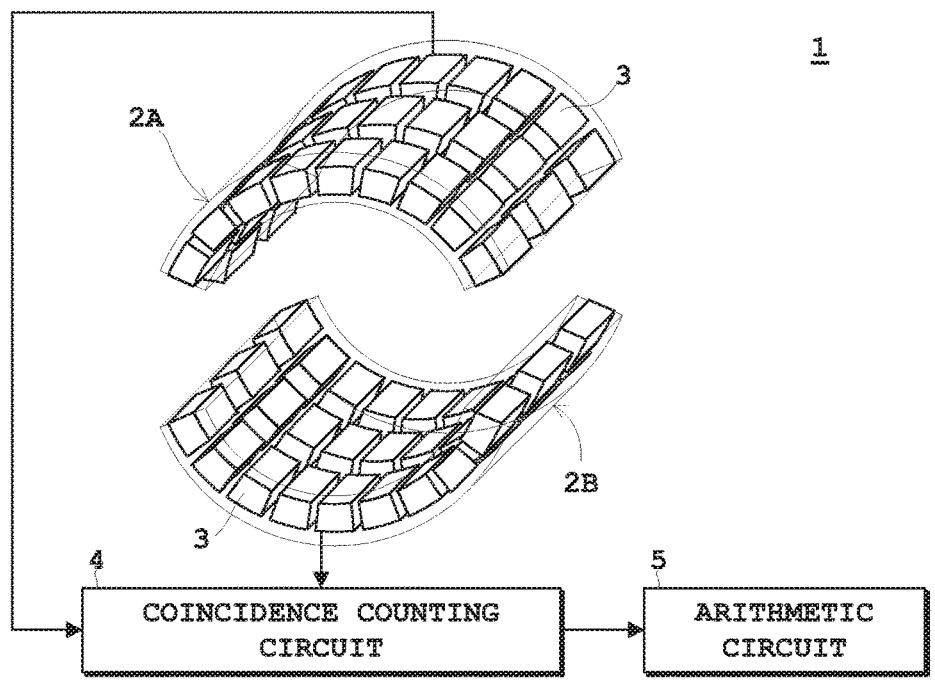
FIG. 1 is an outline perspective view and block diagram showing one mode of a gamma-ray detector arrangement of a partial ring type PET apparatus according to each embodiment.
Figure 2:
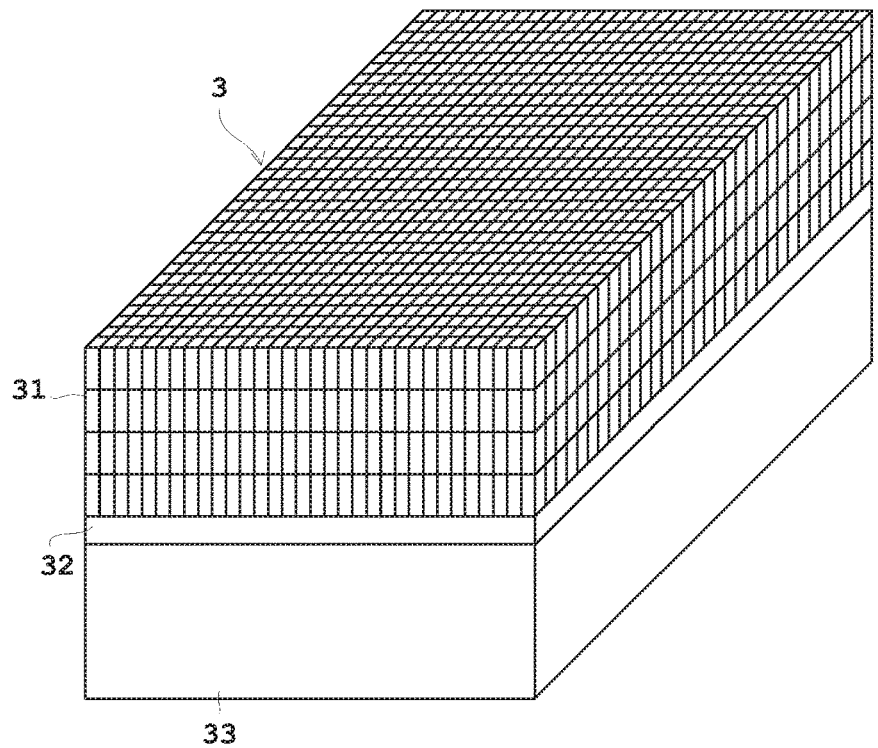
FIG. 2 is an outline perspective view of a gamma-ray detector.

Embodiment 1 of this invention will be described hereinafter with reference to the drawings. FIG. 1 is an outline perspective view and block diagram showing one mode of a gamma-ray detector arrangement of a partial ring type PET apparatus according to each embodiment. FIG. 2 is an outline perspective view of a gamma-ray detector. In this Embodiment 1, including also Embodiments 2 and 3 described hereinafter, a positron emission tomographic apparatus (PET apparatus) will be described as an example of radiation detecting apparatus. FIGS. 1 and 2 show a construction common to each embodiment.

As shown in FIG. 1, a partial ring type PET apparatus has detector units 2A and 2B. The detector units 2A and 2B have a plurality of gamma-ray detectors 3 embedded therein. The partial ring type PET apparatus corresponds to the radiation detecting apparatus in this invention, and corresponds also to the positron emission tomographic apparatus in this invention. The detector units 2A and 2B correspond to the detector units, and the gamma-ray detectors 3 correspond to the radiation detectors in this invention.

The detector units 2A and 2B are constructed to have opened space. That is, the detector units 2A and 2B have therebetween open areas (aperture areas) where the gamma-ray detectors 3 do not exist. In the case of FIG. 1, since the open areas (aperture areas) exist along YZ plane (see FIGS. 4 and 5), the detector units 2A and 2B have an up-down arrangement type geometry. Of course, the open areas (aperture areas) are not limited to the direction of YZ plane, but the gamma-ray detectors 3 may be arranged so that the open areas (aperture areas) exist along a direction of XZ plane (with the detector units 2A and 2B having a right-left arrangement geometry at this time). The gamma-ray detectors 3 may be arranged so that the open areas (aperture areas) exist along planes other than the YZ plane and XZ plane.

In addition, the partial ring type PET apparatus 1 has a coincidence counting circuit 4 and an arithmetic circuit 5. FIG. 1 shows only two connections from the gamma-ray detectors 3 to the coincidence counting circuit 4, but in practice a total number of channels of photomultiplier tubes (PMT) 33 (see FIG. 2) of the gamma-ray detectors 3 is connected to the coincidence counting circuit 4.

A scintillator block 31 (see FIG. 2) of gamma-ray detector 3 converts into light, gamma rays generated from a subject (not shown) medicated with a radioactive drug. The photomultiplier tubes (PMT) 33 (see FIG. 2) of gamma-ray detector 3 multiply and convert the converted light into electric signals. The electric signals are sent into the coincidence counting circuit 4.

Specifically, when the subject (not shown) is medicated with the radioactive drug, two gamma rays are generated by annihilation of positrons from positron emission type RI. The coincidence counting circuit 4 checks positions in the scintillator block 31 (see FIG. 2) and incident times of the gamma rays. Only when the gamma rays are incident simultaneously on two scintillator blocks 31 at opposite sides of the subject, the inputted electric signals are determined to be proper data. When a gamma ray is incident on only one scintillator block 31, the coincidence counting circuit 4 rejects the signal. That is, the coincidence counting circuit 4, based on the above electric signals, detects a simultaneous observation (i.e. coincidence) of gamma rays in two gamma-ray detectors 3.

The electric signals sent into the coincidence counting circuit 4 are sent into the arithmetic circuit 5. The arithmetic circuit 5 executes steps S1-S6 (see FIG. 3) described hereinafter, to perform a reconstruction process for reconstructing, from a measurement data set (measurement data of count values here, that is count data in each embodiment) of the subject (not shown) obtained by the partial ring type PET apparatus 1, a physical quantity distribution (radioactivity distribution image here) of the subject relating to an occurrence factor (generation of gamma rays by medication of the radioactive drug here) of the measurement data set as a multidimensional digital image (reconstruction image here). Specific functions of the arithmetic circuit 5 will be described hereinafter.

The gamma-ray detector 3, as shown in FIG. 2, includes the scintillator block 31, a light guide 32 optically coupled to the scintillator block 31, and the photomultiplier tubes (hereinafter abbreviated as "PMT") 33 optically coupled to the light guide 32. Each scintillator element constituting the scintillator block 31 emits light in response to incidence of a gamma ray to convert the gamma ray into light. The scintillator element detects the gamma ray through this conversion. The light emitted from the scintillator element is fully diffused in the scintillator block 31, and is inputted to the PMT 33 through the light guide 32. The PMT 33 multiplies the light converted by the scintillator block 31, and converts it into electric signals. The electric signals are sent into the coincidence counting circuit 4 (see FIG. 1) as pixel values.

The gamma-ray detector 3, as shown in FIG. 2, is a DOI detector formed of scintillator elements arranged in three dimensions and having a plurality of layers in the depth direction. FIG. 2 shows a DOI detector of four layers, but the number of layers is not particularly limitative as long as it is plural.

Here, the DOI detector is constructed by stacking the respective scintillator elements in the depth direction of radiation. Coordinates information of a depth direction of interaction (DOI: Depth of Interaction) and a transverse direction (direction parallel to the plane of incidence) is derived from gravity center calculations. The spatial resolution in the depth direction can be further improved by using the DOI detector. Therefore, the number of layers of the DOI detector is the number of layers of scintillator elements stacked in the depth direction. In Embodiment 2 described hereinafter, weight coefficients described hereinafter are set based on detection depth position information on the detector elements (scintillator elements) of the DOI detector.

Figure 3:
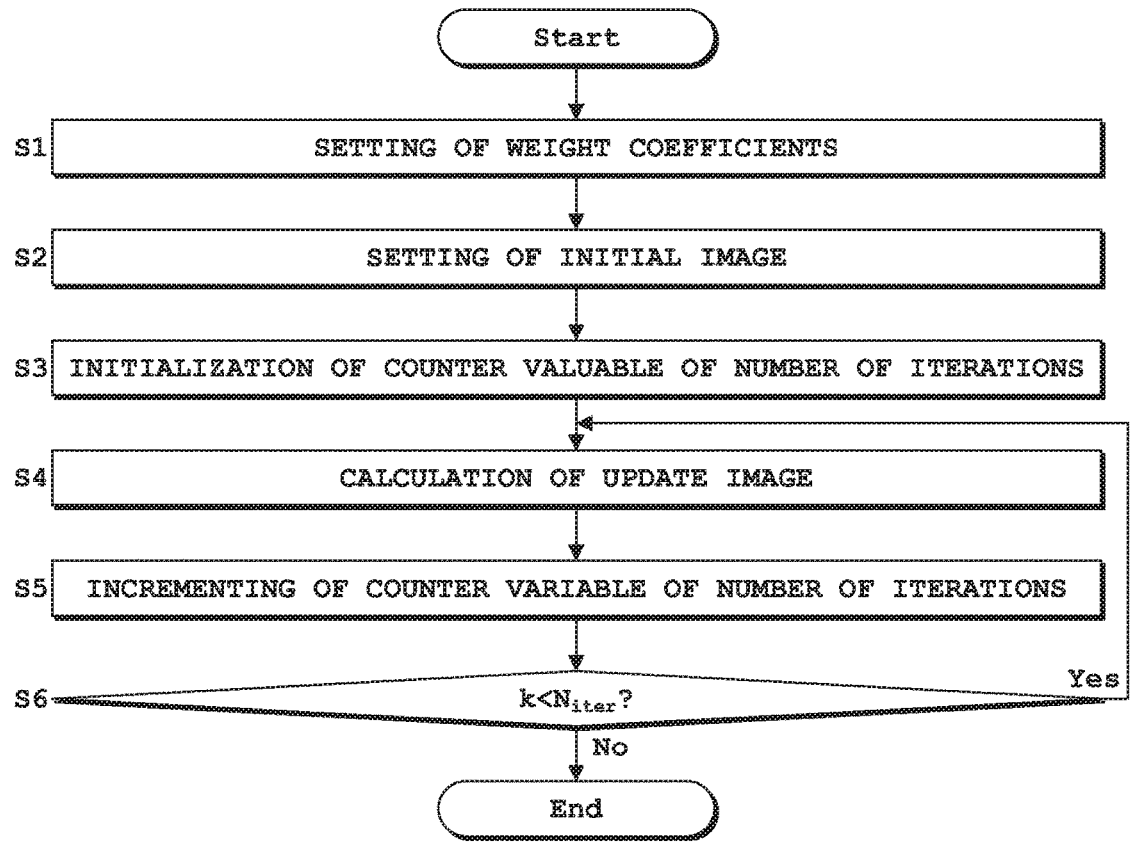
FIG. 3 is a flow chart of an image reconstruction process according to Embodiment 1.
Figure 4:
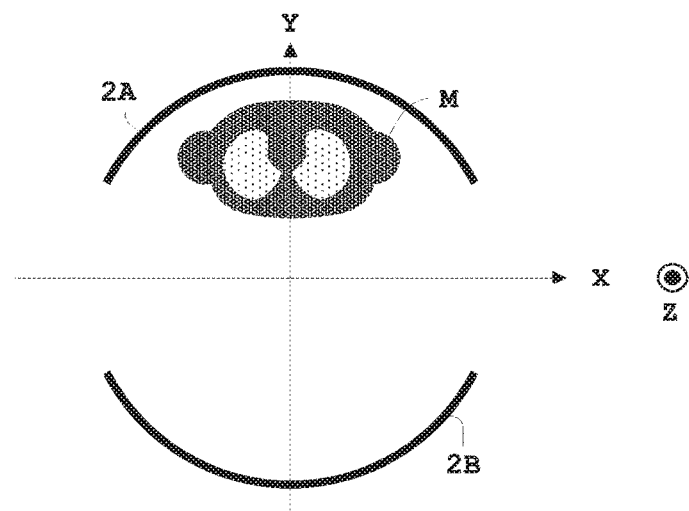
FIG. 4 is a schematic outline front view of detector units of the partial ring type.
Figure 5:
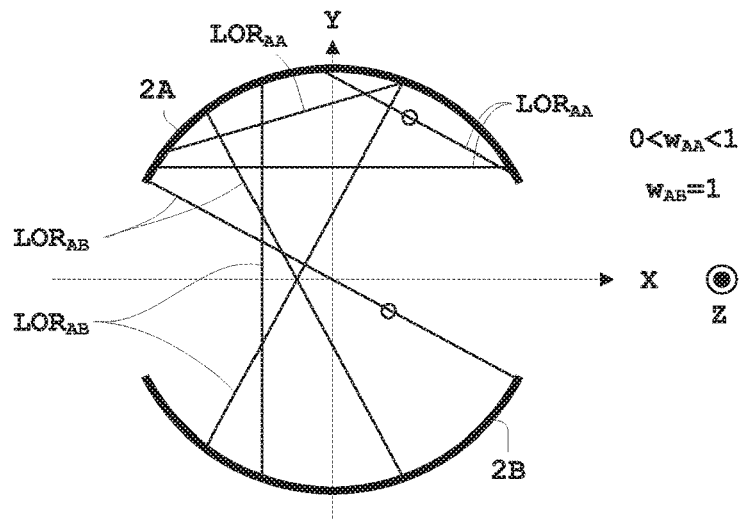
FIG. 5 is a schematic view showing a relationship between the detector units of the partial ring type and setting of weight coefficients.
Figure 6:
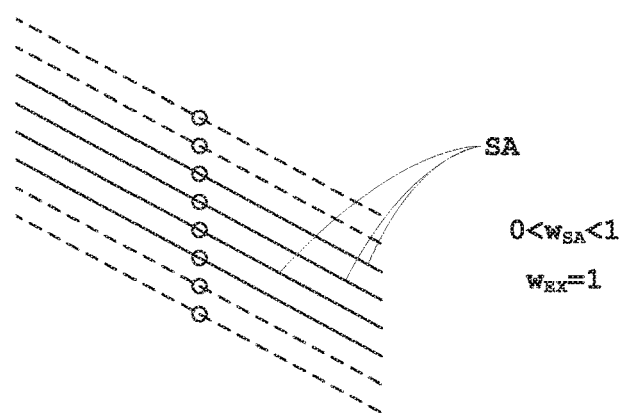
FIG. 6 is a schematic view showing a relationship between streak artifacts and setting of weight coefficients.

Next, the specific functions of the arithmetic circuit 5 will be described with reference to FIGS. 3-6. FIG. 3 is a flow chart of an image reconstruction process according to Embodiment 1. FIG. 4 is a schematic outline front view of the detector units of the partial ring type. FIG. 5 is a schematic view showing a relationship between the detector units of the partial ring type and setting of weight coefficients. FIG. 6 is a schematic view showing a relationship between streak artifacts and setting of weight coefficients.

Before description of the flow chart of FIG. 3, setting of weight coefficients will be described first. As described with reference to FIG. 1 also, the detector units 2A and 2B are in the up-down arrangement type geometry. Because of an arrangement of a top board and a bed (neither being shown) on which a subject M is placed, as shown in FIG. 4, the subject M is located adjacent the upper detector unit 2A. In this embodiment, as shown in FIGS. 1 and 4, the gamma-ray detector 3 (not shown in FIG. 4) is constructed of a plurality of detector units (two detector units 2A and 2B in FIGS. 1 and 4) separated from each other.

When such detector units 2A and 2B of the partial ring type are used, and when image reconstruction is performed by a conventional ML reconstruction method, linear noises (streak artifacts) appear along straight line directions connecting between the detector elements (scintillator elements) of the same detector unit. Particularly when the subject M is placed adjacent the upper detector unit 2A as shown in FIG. 4, streak artifacts appear along the straight line directions connecting between the detector elements (scintillator elements) in the same detector unit 2A.

Then, the streak artifacts can be suppressed by executing steps S1-S6 described hereinafter, in which the count data measured in the pairs of detector elements (scintillator elements) in the same detector unit 2A is multiplied by a weight coefficient smaller than the count data of pairs of detector elements (scintillator elements) in the detector units 2A and 2B different from each other. Element data constituting the measurement data set (measurement data, i.e. count data) is i-th measurement data points in this Embodiment 1, including also Embodiments 2 and 3 described hereinafter.

As shown in FIG. 5, the straight line directions connecting between detector elements (scintillator elements) in the same detector unit 2A are labeled $LOR_{AA}$. A weight coefficient for the element data (i-th measurement data points) along the straight line directions $LOR_{AA}$ is labeled $w_{AA}$. The straight line directions connecting between detector elements (scintillator elements) in the detector units 2A and 2B different from each other are labeled $LOR_{AB}$. A weight coefficient for the element data (i-th measuring data points) in the straight line directions $LOR_{AB}$ is labeled $w_{AB}$. At this time, the weight coefficient $w_{AA}$ for the element data (i-th measurement data points) along the straight line directions $LOR_{AA}$ connecting between the detector elements (scintillator elements) in the same detector unit 2A is set smaller than the weight coefficient $w_{AB}$ for the element data (i-th measuring data points) along the straight line directions $LOR_{AB}$ connecting between the detector elements (scintillator elements) in the detector units 2A and 2B different from each other.

Since weight coefficients generally are larger than 0 and are 1 or less, the weight coefficient $w_{AA}$ is set to a value larger than 0 and smaller than 1 ($0<w_{AA}<1$), and the weight coefficient $w_{AB}$ is set to 1 ($w_{AB}=1$). The straight line directions $LOR_{AA}$ are not only one straight line direction connecting between detector elements (scintillator elements) in the same detector unit 2A; various straight line directions corresponding to straight line directions connecting between detector elements (scintillator elements) in the same detector unit 2A will make the straight line directions $LOR_{AA}$. Similarly, the straight line directions $LOR_{AB}$ are not only one straight line direction connecting between detector elements (scintillator elements) in the detector units 2A and 2B different from each other; various straight line directions corresponding to straight line directions connecting between detector elements (scintillator elements) in the detector unit 2A and 2B different from each other will make the straight line directions $LOR_{AB}$.

Note here that "the weight coefficient $w_{AA}$ for the element data (i-th measurement data points) along the straight line directions $LOR_{AA}$ connecting between detector elements (scintillator elements) in the same detector unit 2A . . . is set to a value larger than 0 and smaller than 1" means that the weight coefficient $w_{AA}$ applied to the straight line directions $LOR_{AA}$ is set to a value larger than 0 and smaller than 1. That is, even if parallel to the straight line direction $LOR_{AA}$ as shown in FIG. 5 (see ○ in FIG. 5), the straight line direction $LOR_{AB}$ (see ○ in FIG. 5), although parallel to that straight line direction $LOR_{AA}$, may extend between detector elements (scintillator elements) in the detector units 2A and 2B different from each other, in which case the weight coefficient $w_{AB}$ applied to this straight line direction $LOR_{AB}$ is set to 1.

Instead of being limited to the detector units 2A and 2B separated from each other, with one detector unit, if it is a detector unit constructed to have opened space, gamma-rays passing through the opening part (cutout portion) are not detected. Therefore, the partial loss of projection data causes noises of strong spatial correlation (e.g. streak artifacts) on a reconstruction image. Therefore, with the streak artifacts referenced SA as shown in FIG. 6, the streak artifacts SA which are linear noises may be considered due to a reconstruction process performed using partial functions, without setting weight coefficients, as in conventional practice. So, when weight coefficients are set to constants which do not depend on the element data (i-th measurement data points), the weight coefficients may be set based on the directionality of the streak artifacts SA produced on the reconstruction image.

Assume that the solid lines shown in FIG. 6 are streak artifacts SA, and that the broken lines shown in FIG. 6 are straight lines parallel to the streak artifacts SA (see ○ in FIG. 6) but are straight lines (see ○ in FIG. 6) not corresponding to the streak artifacts SA. A weight coefficient for the element data (i-th measurement data points) along the running direction of the streak artifacts SA is labeled $w_{SA}$. A weight coefficient for the element data (i-th measurement data points) not along the streak artifacts SA, including the broken lines shown in FIG. 6, is labeled $w_{EX}$. At this time, the weight coefficient $w_{SA}$ for the element data (i-th measurement data points) along the running direction of the streak artifacts SA is set smaller than the weight coefficient $w_{EX}$ for the element data (i-th measurement data points) not along the streak artifacts SA, thereby relatively to lessen the influence of the measurement data set (measurement data) along the streak artifacts SA.

Since weight coefficients generally are larger than 0 and are 1 or less as noted hereinbefore, the weight coefficient $w_{SA}$ is set larger than 0 and smaller than 1 ($0<w_{SA}<1$), and the weight coefficient $w_{EX}$ is set to 1 ($w_{EX}=1$). Note here that "the weight coefficient $w_{SA}$ for the element data (i-th measurement data points) along the running direction of the streak artifacts SA is set larger than 0 and smaller than 1" means that the weight coefficient $w_{SA}$ applied to the streak artifacts SA is set to a value larger than 0 and smaller than 1. That is, in the case of the straight lines not corresponding to the streak artifacts SA (see the broken lines in FIG. 6) even if parallel to the streak artifacts SA as shown in FIG. 6, the weight coefficient applied to these straight lines is regarded as weight coefficient $w_{EX}$ for the element data (i-th measurement data points) not along the streak artifacts SA, which weight coefficient $w_{EX}$ is set to 1.

As is clear from the above reason, the weight coefficients set in this way are non-negative coefficients (influence adjusting coefficients) for adjusting influence rates of the element data (i-th measurement data points) on reconstruction images. Therefore, the weight coefficients set in this way are also weight coefficients of back projection for reconstruction images of the element data (i-th measurement data points). These weight coefficients are used to weight the partial functions described hereinafter. When application is made to nuclear medicine diagnostic apparatus (emission CT apparatus) represented by a positron emission tomographic apparatus (PET apparatus) as in this Embodiment 1, including also Embodiments 2 and 3 described hereinafter, an error distribution of the element data (i-th measurement data points) which constitute the measurement data set (measurement data) is Poisson distribution, and the data function is a likelihood function. Therefore, the likelihood function of Poisson distribution is weighted.

The likelihood function for which weighting has been performed will be called hereinafter the "weighted likelihood function". Where the measurement data set (measurement data) is sinogram data or histogram data, with the weighted likelihood function of Poisson distribution labeled L(x) as in conventional practice, the weighted likelihood function L(x) of Poisson distribution is expressed by the following equation (2):

[Math 2]

$$L(x) = \sum_{i=1}^{I} w_i a_i \cdot x - \sum_{i=1}^{I} w_i y_i \log(a_i \cdot x + r_i) \quad (2)$$

$$= \sum_{i=1}^{I} [w_i a_i \cdot x - w_i y_i \log(a_i \cdot x + r_i)]$$

Here, as in the conventional case (1) given hereinbefore, x is a reconstructed image vector (however, pixel values are non-negative), I is the number of measurement data points, $a_i$ is a sensitivity distribution function at an i-th measurement data point (an i-th row vector of system matrix A), $y_i$ is a prompt coincidence value (count value) at the i-th measurement data point, and $r_i$ is estimated values of count values of coincidences (random coincidences and scatter coincidences) other than the prompt coincidence value (count value) at the i-th measurement data point. Further, $w_i$ in equation (2) above is a weight coefficient (likelihood weight coefficient) for the i-th measurement data point.

The difference between the conventional likelihood function (equation (1) above) and the weighted likelihood function (equation (2) above) lies in that the weight coefficient $w_i$ is applied to weight each measurement data point. That is, the role of the likelihood weight coefficient is to adjust the influence rate of each measurement data point on the reconstruction image. When $\Sigma$ on the right side of equation (2)

above is bundled with the whole, "$w_i a_i \cdot x - w_i y_i \log(w_i a_i + r_i)$", which is the contents of $\Sigma$ on the right side of equation (2) above, can be defined as a partial function composed based on the error distribution of element data (i-th measurement data points). That is, the data function (likelihood function in each embodiment) is expressed by a sum of partial functions composed based on the error distribution of element data (i-th measurement data points) from equation (2) above. Assuming that a multivariate function in which a digital image after a reconstruction process is regarded as unknown is a "first multivariate function", the first multivariate function is a data function (likelihood function).

A reconstruction process is performed based on optimization calculations of the weighted likelihood function in equation (2) above, which is weighted in this way. Specifically, the weighted likelihood function of equation (2) above can be maximized by the repeated calculation algorithm (iterative method) shown below, which can acquire a digital image after the reconstruction process. A specific reconstruction process is shown in FIG. 3.

(Step S1) Setting of Weight Coefficients

In equation (2) above, likelihood weight coefficients $w_i$ are set to all the data points. Specifically, in this Embodiment 1, $w_i = \alpha$ ($0<\alpha<1$) is applied to data points provided by pairs of detector elements (scintillator elements) within the same detector unit 2A, and $w_i = 1$ to the other data points.

(Step S2) Setting of Initial Image

A non-negative image is regarded as an initial image $x^{(0)}$. When application is made to nuclear medicine diagnostic apparatus (emission CT apparatus) represented by a positron emission tomographic apparatus (PET apparatus) as in this Embodiment 1, including also Embodiments 2 and 3 described hereinafter, 0 is excluded as $x^{(0)} > 0$. The initial image $x^{(0)}$ may be a reconstruction image having a uniform pixel value, for example.

(Step S3) Initialization of Counter Variable of Number of Iterations

The counter variable of the number of iterations in the repeated calculation algorithm (iterative method) is labeled k, and counter variable k of the number of iterations is initialized (k=0).

(Step S4) Calculation of Update Image

An update image $x^{(k+1)}$ of a (k+1)th time is calculated using the following equation (3). In that equation, J is the number of pixels in the reconstruction image. As is clear from the following equation (3), the likelihood weight coefficient $w_i$ is applied also to the following equation (3) in order to maximize the weighted likelihood function in equation (2) above.

[Math 3]

$$x_j^{(k+1)} = \frac{x_j^{(k)}}{\sum_{i=1}^{I} w_i a_{ij}} \sum_{i=1}^{I} \frac{w_i a_{ij} y_i}{\sum_{j'=1}^{J} a_{ij'} x_{j'}^{(k)} + r_i} \quad (j = 1, \ldots, J) \quad (3)$$

(Step S5) Incrementing of Counter Variable of Number of Iterations

The counter variable k is incremented (k←k+1). Note that "k←k+1" means substituting (k+1) on the right side fork on the left side.

(Step S6) $k < N_{iter}$ ?

The number of iterations which ends the repeated calculation algorithm is set to $N_{iter}$, and it is determined whether or not the counter variable k has reached the number of iterations $N_{iter}$. The number of iterations $N_{iter}$ may be set beforehand by the user. When $k < N_{iter}$, the operation returns to step S4 in order to continue the repeated calculation algorithm. When $k = N_{iter}$, it is noted that the repeated calculation algorithm is completed, to end the series of calculations.

The update image $x^{(k+1)}$ obtained in this way is acquired as reconstruction image. Instead of setting the number of iterations $N_{iter}$, the user may observe an update image $x^{(k+1)}$ obtained from each updating, the user many stop the repeated calculation algorithm based on an observation result, and the update image $x^{(k+1)}$ then obtained may be acquired as reconstruction image. As described above, steps S1-S6 correspond to the reconstruction processing steps in this invention.

The image reconstruction processing method according to this Embodiment 1 is characterized by adding weight to the conventional reconstruction processing steps. That is, weighting is performed when performing the reconstruction process based on optimization calculations of a multivariate function in which a digital image is unknown, and which consists of a data function generalized from the likelihood function of the Poisson distribution in Nonpatent Document 1. Assuming that the multivariate function in which the digital image is unknown is a "first multivariate function" as noted hereinbefore, the first multivariate function in this Embodiment 1 is a data function (likelihood function in each embodiment) expressed by a sum of partial functions ("$w_i a_i \cdot x - w_i y_i \log(w_i a_i + r_i)$" in equation (2) above) composed based on an error distribution of element data (i-th measurement data points in each embodiment) constituting the measurement data set (measurement data of count values here, i.e. measurement data in each embodiment) of the subject M obtained by the radiation detecting apparatus (partial ring type PET apparatus 1 in each embodiment). And the partial functions are weighted with weight coefficients of back projection to the reconstruction image of the element data (i-th measurement data points) corresponding to the partial functions noted above. These weight coefficients are non-negative coefficients (also called "influence adjusting coefficients") which adjust the influence rates of element data (i-th measurement data points) on the reconstruction image as noted above, By weighting the partial functions with these weight coefficients, artifacts appearing on the image can be suppressed, and the spatial resolution of the image can be improved.

In this Embodiment 1, including also Embodiments 2 and 3 described hereinafter, the radiation detecting apparatus is a positron emission tomographic apparatus (PET apparatus). When the radiation detecting apparatus is a PET apparatus as in each embodiment, or either a single photon emission tomographic apparatus (SPECT apparatus) or an X-ray computerized tomographic apparatus (X-ray CT apparatus), and when linear noises (streak artifacts) occur, it is thought due to the reconstruction process being performed using the partial functions without setting weight coefficients, as in conventional practice. So, the linear noises (streak artifacts) can be suppressed by setting a weight coefficient based on the directionality of the linear noises appearing on the reconstruction image when the weight coefficient is a constant independent of element data (i-th measurement data points).

More particularly, the weight coefficient $w_{SA}$ (weight coefficient larger than 0, however) for the element data (i-th measurement data points) along the running direction of the linear noises (streak artifacts SA in FIG. 6) is set to a value smaller than the weight coefficient $w_{EX}$ (weight coefficient larger than 0) for the element data (i-th measurement data points) not along the running direction of the linear noises (streak artifacts SA) (e.g. $0<w_{SA}<1$, $w_{EX}=1$). This relatively lessens the influence of the measurement data set (measurement data) along the linear noises (streak artifacts SA). As a result, the linear noises (streak artifacts SA) can be suppressed.

The above linear noises (streak artifacts) occur more easily when detector units constructed to have opened space are used rather than full ring type detector units. In the case of the detector units constructed to have opened space, radiation passing through the opened space (omission portion) is not detected. Therefore, the partial loss of projection data causes noise having strong spatial correlation on the reconstruction image. Particularly when, as in this Embodiment 1, including also Embodiments 2 and 3 described hereinafter, a plurality of detector units (two detector units 2A and 2B in FIGS. 1 and 4) separated from each other are used, the linear noises (streak artifacts) are thought to occur along the straight line direction connecting between detector elements in the same detector unit.

Then, the viewpoint is changed, and when the radiation detectors (gamma-ray detectors 3 in each embodiment) constituting the radiation detecting apparatus (partial ring type PET apparatus 1) are constructed of a plurality of detector units (two detector units 2A and 2B) separated from each other, the weight coefficient (weight coefficient larger than 0, however) for the element data (i-th measurement data points) along the straight line directions connecting between detector elements in the same detector unit is set to a value (e.g. $0<w_{AA}<1$, $w_{AB}=1$) smaller than the weight coefficient (weight coefficient larger than 0) for the element data (i-th measurement data points) along the straight line directions connecting between the detector elements in the mutually different detector units. This can suppress the linear noises (streak artifacts) appearing along the straight line directions connecting between the detector elements in the same detector unit.

When the radiation detecting apparatus is the PET apparatus as in each embodiment, or when it is a SPECT apparatus, the measurement data set (measurement data) of the subject M obtained by the radiation detecting apparatus (partial ring type PET apparatus 1) is either sinogram data, histogram data or list mode data. Particularly when the measurement data set (measurement data) is sinogram data or histogram data, the weighted likelihood function L(x) of Poisson distribution is expressed by equation (2) above in this Embodiment 1.

In this Embodiment 1, including also Embodiments 2 and 3 to be described hereinafter, the error distribution of the element data (i-th measurement data points) constituting the measurement data set (measurement data) is Poisson distribution. The error distribution, when it is Poisson distribution, is used with a nuclear medicine diagnostic apparatus (emission CT apparatus) represented by a PET apparatus, for example.

EMBODIMENT 2

Figure 7:
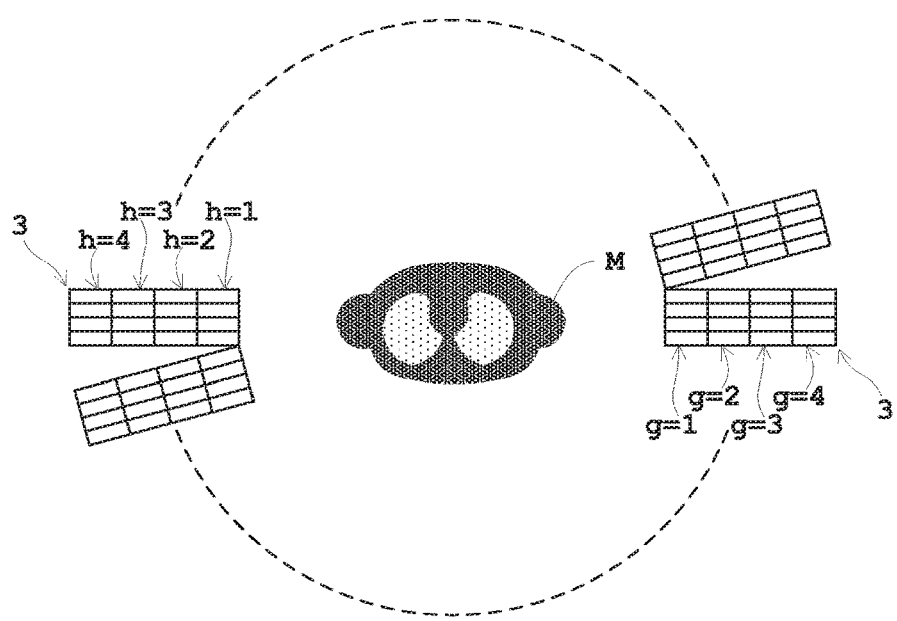
FIG. 7 is a schematic view showing a relationship between a four-layer (four-stage) DOI detectors and stage numbers of detection depths.

Next, Embodiment 2 of this invention will be described with reference to the drawings. FIG. 7 is a schematic view showing a relationship between four-layer (four-stage) DOI detectors and stage numbers of detection depth. FIG. 8(a) is a table showing an example of likelihood weight coefficients for pairs of DOI layers. FIG. 8(b) is a graph, when the stage numbers of detection depths are discrete variables and one of the discrete variables is fixed, showing a nonincreasing function of the weight coefficient for the other variable For simplicity of illustration, FIG. 7 shows only scintillator blocks 31 (see FIG. 2) about the gamma-ray detectors 3 consisting of the DOI detectors, leaving out the other aspects of the construction, namely the light guides 32 and PMT 33 (see FIG. 2 for both), and shows only four of the scintillator blocks 31 in the transverse direction.

In Embodiment 1 described above, the weight coefficients are set based on the directionality of the linear noises appearing on the reconstruction image when the weight coefficients are set to constants which do not depend on the element data (i-th measurement data points). In this Embodiment 2, on the other hand, weight coefficients are set based on detection depth position information of the detector elements (scintillator elements) of the DOI detectors.

Specifically, with a PET apparatus (DOI-PET apparatus) having DOI detectors with detector elements (scintillator elements) stacked in multiple stages in the depth direction as shown in FIG. 2, of a detecting element pair close to the object of measurement (shallow DOI layer) and a faraway detecting element pair (deep DOI layer), the latter has the larger range of sensitivity distribution function, and hence the latter has a lower degree of reliability than the former. So, the spatial resolution of image is improved by setting weight coefficients depending on the detection depth position information corresponding to the measurement data set (measurement data).

Figure 8:
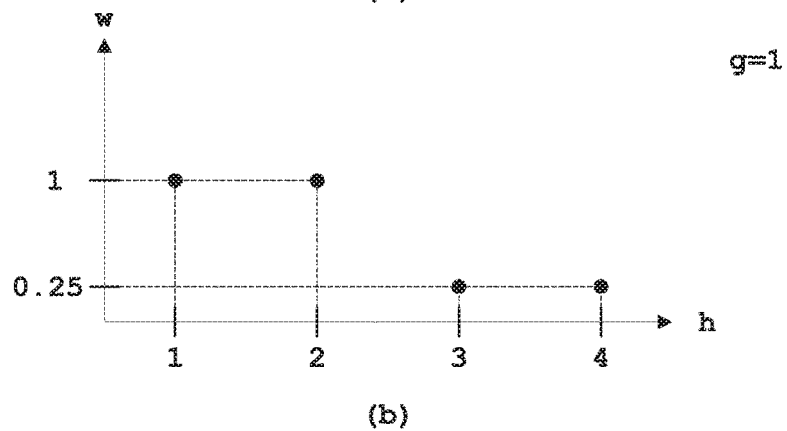
FIG. 8(*a*) is a table showing an example of likelihood weight coefficients for pairs of DOI layers, and (*b*) is a graph, when the stage numbers of detection depths are discrete variables and one of the discrete variables is fixed, showing a nonincreasing function of the weight coefficient for the other variable.

When N is a natural number larger than or equal to 2, N=4 is assumed in FIGS. 7 and 8, and the gamma-ray detectors 3 are constructed to measure detection depth position information of four stages (i.e. four layers). That is, the gamma-ray detectors 3 are constructed of four-layer DOI detectors. Stage numbers of detection depth of two detector elements (scintillator elements) having measured a coincidence are set to g and h ($1\leq g$, $h\leq N$), respectively, so that the numbers are progressively larger from shallow stage to deep stage. Since N=4 in FIGS. 7 and 8, g=1, 2, 3 and 4 and h=1, 2, 3 and 4 from shallow stage to deep stage as shown in FIG. 7. As described in FIG. 2 of Embodiment 1. There is no particular limitation to the stage numbers (i.e. layer numbers) of the DOI detectors as long as they are natural numbers larger than or equal to 2 (i.e. plural numbers).

Since the stage numbers g and h are natural numbers, assuming that the stage numbers g and h are discrete variables, weight coefficient w is expressed by a two-dimensional function having the stage numbers g and h as discrete variables. Since reliability in the count data measured by a pair in a deep DOI layer is lower than reliability in the count data measured by a pair in a shallow DOI layer as noted hereinbefore, weight coefficients w are set such that the weight coefficient w for the pair in the deep DOI layer is smaller than the weight coefficient w for the pair in the shallow DOI layer. When h=1, 2, 3 and 4 and g=1, 2, 3 and 4 from shallow stage to deep stage as shown in FIG. 7, and when one variable g is fixed, the two-dimensional function about weight coefficient w is expressed by a one-dimensional function for the other variable h and the one-dimensional function makes a nonincreasing function. Conversely, also when variable h is fixed, the two-dimensional function about weight coefficient w is expressed by a one-dimensional function for the other variable g and the one-dimensional function makes a nonincreasing function.

FIG. 8(a) shows an example of likelihood weight coefficients for pairs in the DOI layers. When one variable g is fixed to 1, the two-dimensional function about weight coefficient w is expressed by the one-dimensional function for the other variable h as shown in FIG. 8(b). And the one-dimensional function is a nonincreasing function, with weight coefficient w being 1 (written "1.00" in FIG. 8(a)) when h=1 and 2, and weight coefficient w being 0.25 when h=3 and 4.

The weight coefficient is not limited to the values shown in FIG. 8. In FIG. 8, the weight coefficients for h=1 and 2 when g is fixed are set to the same value, the weight coefficients for h=3 and 4 when g is fixed are set to the same value, the weight coefficients for g=1 and 2 when h is fixed are set to the same value, and the weight coefficients for g=3 and 4 when h is fixed are set to the same value. However, the weight coefficients may be any nonincreasing function set to decrease by stages with each increase in the value of g and h.

In FIG. 8, the one-dimensional function (nonincreasing function) for the other variable obtained when one variable is fixed is the same as the one-dimensional function (nonincreasing function) for one variable obtained when the other variable is fixed, but they do not necessarily need to be the same. The one-dimensional function (nonincreasing function) for the other variable obtained when one variable is fixed and the one-dimensional function (nonincreasing function) for one variable obtained when the other variable is fixed may be set to mutually different functions according to the characteristic of each gamma-ray detector 3.

The weight coefficients set in this way are applied to equation (2) above as in foregoing Embodiment 1. The weighted likelihood function of equation (2) above can be maximized by the repeated calculation algorithm (iterative method) shown below, which can acquire a digital image after the reconstruction process, as in foregoing Embodiment 1. A specific reconstruction process is shown in FIG. 3, as in foregoing Embodiment 1. Regarding the signs of the steps in this Embodiment 2, the same signs (S1-S6) of the steps as in foregoing Embodiment 1 are affixed.

(Step S1) Setting of Weight Coefficients

In equation (2) above, likelihood weight coefficients $w_i$ are set to all the data points. The difference from foregoing Embodiment 1 lies in that this Embodiment 2 sets weight coefficients based on the detection depth position information of the detector elements (scintillator elements) of the DOI detectors as described above. As shown in FIGS. 2 and 7, for example, in the case of the DOI detectors of four layers (four stages), the likelihood weight coefficients shown in FIG. 8 are set to pairs in each DOI layer.

(Step S2)-(Step S6)

Since steps S2-S6 are the same as steps S2-S6 in foregoing embodiment 1, their description is omitted. As described above, steps S1-S6 correspond to the reconstruction processing steps in this invention.

The image reconstruction processing method according to this Embodiment 2, as in Embodiment 1 described hereinbefore, weighting is performed when performing the reconstruction process based on optimization calculations of a multivariate function in which a digital image is unknown, and which consists of a data function (likelihood function in each embodiment). And partial functions ("$w_i a_i \cdot x - w_i y_i \log (w_i a_i + r_i)$" in equation (2) above) are weighted with weight coefficients of back projection to the reconstruction image of the element data (i-th measurement data points in each embodiment) corresponding to the partial functions, thereby to be able to improve the spatial resolution of the image.

In the Embodiment 2, as in Embodiment 1 described hereinbefore and Embodiment 3 described hereinafter, the radiation detecting apparatus is a positron emission tomographic apparatus (PET apparatus). When the radiation detecting apparatus is a PET apparatus as in each embodiment, or a SPECT apparatus, the measurement data set (here, measurement data of count values, i.e. count data in each embodiment) of the subject M obtained by the radiation detecting apparatus (partial ring type PET apparatus 1 in each embodiment) is either sinogram data, histogram data or list mode data. Particularly when the measurement data set (measurement data) is sinogram data or histogram data, the weighted likelihood function L(x) of Poisson distribution is expressed by equation (2) above in this Embodiment 2, as described in foregoing Embodiment 1.

When the radiation detecting apparatus is a PET apparatus as in each embodiment, or a SPECT apparatus, and when deterioration occurs in the spatial resolution of the image, it is thought due to the reconstruction process being performed using partial functions without setting weight coefficients, as in conventional practice. Particularly when the radiation detectors (gamma-ray detectors 3 in each embodiment) constituting the radiation detecting apparatus are constructed to measure detection depth position information on radiation, that is, when the DOI detectors are used which are constructed by stacking each detecting element in the depth direction of radiation, the following phenomenon happens. That is, of a detecting element pair close to the object of measurement (shallow DOI layer) and a faraway detecting element pair (deep DOI layer), the latter has the larger range of sensitivity distribution function, and hence the latter has a lower degree of reliability than the former. So, the spatial resolution of image can be improved by setting weight coefficients depending on the detection depth position information corresponding to the measurement data set (measurement data).

More particularly, when N is a natural number larger than or equal to 2 (N=4 in FIGS. 7 and 8), the radiation detectors (gamma-ray detectors 3) are constructed to measure detection depth position information of N stages (four stages) (that is, constructed of DOI detectors). In the detector elements constituting the radiation detectors (gamma-ray detectors 3), stage numbers of detection depth of two detector elements (scintillator elements) having measured a coincidence are set to g and h ($1 \leq g$, $h \leq N$), respectively, so that the numbers become larger from shallow stage to deep stage. At this time, the weight coefficient is a two-dimensional function having the stage numbers g and h as discrete variables, the two-dimensional function being such that, when one variable is fixed, a one-dimensional function for the other variable obtained is a nonincreasing function. Consequently, the spatial resolution of the image can be improved by weighting in which count data measured by pairs in deep DOI layers having a low degree of reliability is multiplied by a smaller weight coefficient than count data measured by pairs in shallow DOI layers having a high degree of reliability.

In the Embodiment 2, as in Embodiment 1 described hereinbefore and Embodiment 3 described hereinafter, the error distribution of the element data (i-th measurement data points) constituting the measurement data set (measurement data) is Poisson distribution. The error distribution, when it is Poisson distribution, is used with a nuclear medicine diagnostic apparatus (emission CT apparatus) represented by a PET apparatus, for example.

EMBODIMENT 3

Next, Embodiment 3 of this invention will be described
In foregoing Embodiments 1 and 2, the weighted likelihood function in equation (2) above has been the case where the measuring data is sinogram data or histogram data. In this Embodiment 3, on the other hand, a weighted likelihood function is set when the measurement data is list mode data. Here, the list mode data is data having been saved, in a time series, detecting event information (detector numbers, detection times, energy of gamma rays and so on) acquired with the radiation detectors of the PET apparatus. When the measurement data is list mode data (time series data), weighted likelihood function L(x) of Poisson distribution is expressed by the following equation (4):

[Math 4]

$$L(x) = \sum_{i=1}^{I} w_i a_i \cdot x - \sum_{n=1}^{N} w_{i(n)} y_{i(n)} \log(a_{i(n)} \cdot x + r_{i(n)}) \quad (4)$$

Here, N is the number of events (the number of lists), and i(n) is a number (1≤i(n)≤N) of measurement data point which has measured an n-th event. The weight coefficients set in this way are applied to equation (4) above. The weighted likelihood function of equation (4) above can be maximized by the repeated calculation algorithm (iterative method) shown in FIG. 3 as in foregoing Embodiments 1 and 2, and a digital image after the reconstruction process can be acquired.

Steps S1-S6 shown in FIG. 3 are the same as steps S1-S6 in foregoing Embodiments 1 and 2, and their description is omitted. However, step S4 (calculating of update image) uses the following equation (5) when the data format is the list mode data.

[Math 5]

$$x_j^{(k+1)} = \frac{x_j^{(k)}}{\sum_{i=1}^{I} w_i a_{ij}} \sum_{n=1}^{N} \frac{w_{i(n)} a_{i(n)j} y_{i(n)}}{\sum_{j'=1}^{J} a_{i(n)j'} x_{j'}^{(k)} + r_{i(n)}} \quad (j = 1, \ldots, J) \quad (5)$$

As described above, step S1-S6 correspond to the reconstruction processing steps in this invention.

The functions and effects of the image reconstruction processing method according to this Embodiment 3 are also the same as the functions and effects of the image reconstruction processing method according to foregoing Embodiments 1 and 2, and their description is omitted. Regarding the weight coefficients in equation (4) above, the weight coefficients may be set based on the directionality of linear noises occurring in the reconstruction image when the weight coefficients are constants independent of element data as in foregoing Embodiment 1, or the weight coefficients may be set based on the detection depth position information on the detector elements of the DOI detectors as in foregoing Embodiment 2.

This invention is not limited to the foregoing embodiments, but may be modified as follows:

(1) In each foregoing embodiment, the positron emission tomographic apparatus (PET apparatus) has been described as an example of radiation detecting apparatus. However, there is no limitation if it is an apparatus which acquires measurement data sets of a subject based on detection of radiation. Application may be made to a single photon emission tomographic apparatus (SPECT apparatus), an X-ray computerized tomographic apparatus (X-ray CT apparatus) and the like.

(2) There is no particular limitation to the object of radiography in each foregoing embodiment. In the case of each foregoing embodiment in particular, application may be made to an apparatus for radiographing the whole body of a subject, an apparatus for radiographing the head of a subject, and an apparatus for radiographing the breasts of a subject.

Figure 9:
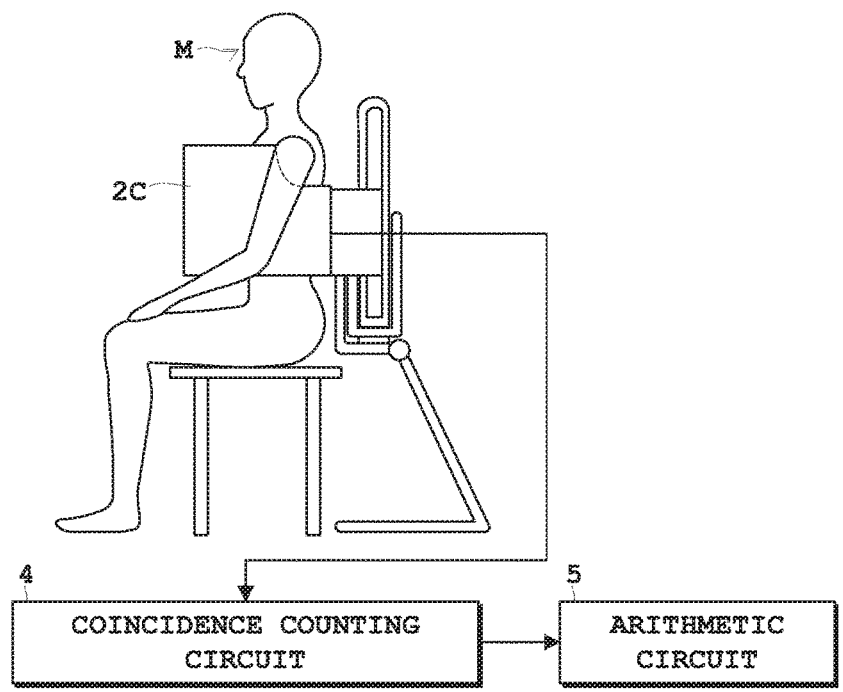
FIG. 9 is a side view and block diagram of a mammographic apparatus according to a modification.

(3) In each foregoing embodiment, it was a partial ring type PET apparatus 1 as shown in FIG. 1, but application may be made to an apparatus like a mammographic apparatus with radiation detectors arranged opposite the breasts of a human body M. It has the same construction as in FIG. 1 except that the detector units 2A and 2B of FIG. 1 are replaced with a breast inspection unit 2C as shown in FIG. 9. In the case of FIG. 9, the breast inspection unit 2C is in the form of a cutout, and this cutout is pinched under the arms for inspection of the breasts. A plurality of gamma-ray detectors 3 (not shown in FIG. 9) are arranged in the breast inspection unit 2C to fit with the cutout.

(4) Each foregoing embodiment has provided DOI detectors, but application may be made to radiation detectors which do not discriminate the depth direction. Particularly when, as in foregoing Embodiment 1, the weight coefficients are constants independent of the element data, and the weight coefficients are set based on the directionality of linear noises occurring in a reconstruction image, the weight coefficients can be set without using detection depth position information on the detector elements of the DOI detectors as in foregoing Embodiment 2.

(5) In each foregoing embodiment, where the radiation detecting apparatus is a positron emission tomographic apparatus (PET apparatus), the PET apparatus (partial ring type PET apparatus 1 in FIG. 1) has the detector units constructed to have opened space. Application may be made to an ordinary full ring type PET apparatus, not necessarily requiring the detector units constructed to have opened space. Particularly when the weight coefficients are set based on the detection depth position information on the detector elements of the DOI detectors as in foregoing Embodiment 2, the weight coefficients can be set without using the directionality of the linear noises as in foregoing embodiment 1.

Figure 10:
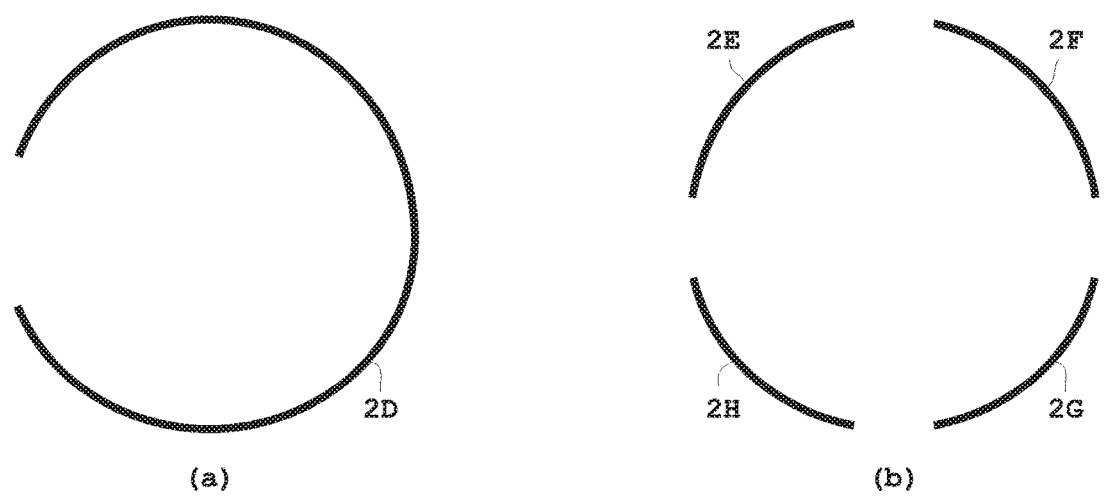
FIGS. 10(*a*) and (*b*) are schematic front views of detector units according to further modifications.

(6) In each foregoing embodiment, where the radiation detecting apparatus is a positron emission tomographic apparatus (PET apparatus), the PET apparatus has two separated detector units 2A and 2B (see FIGS. 1, 4 and 5). However, it may not necessarily be the plurality of detector units separated from each other. As noted in Embodiment 1, one detector unit 2D constructed to have opened space as shown in FIG. 10(a) may serve the purpose.

(7) In each foregoing embodiment, where the radiation detecting apparatus is a positron emission tomographic apparatus (PET apparatus), the PET apparatus has two separated detector units 2A and 2B (see FIGS. 1, 4 and 5). However, the number is not limited to two. As long as they are a plurality of detector units separated from one another, three or more separated detector units will serve the purpose, such as, for example, four detector units 2E, 2F, 2G and 2H separated from one another as shown in FIG. 10(b).

(8) In each foregoing embodiment, the first multivariate function is a data function (likelihood function in each embodiment) expressed by a sum of partial functions composed based on the error distribution of element data (i-th measurement data points in each embodiment) constituting the measurement data set (measurement data) of the subject M obtained by the radiation detecting apparatus (partial ring type PET apparatus 1 in each embodiment). However, the first multivariate function may be a sum of the above data function (likelihood function) and a second multivariate function composed based on prior information on a physical quantity distribution. When the positron emission tomographic apparatus (PET apparatus) is used as in each embodiment, an image reconstructing method is also conceivable which is based on the maximization of L(x)+U(x) which is a sum of the weighted likelihood function L(x) in equation (2) above or equation (4) above and another function U(x) consisting of the second multivariate function composed based on the prior information on a physical quantity distribution. While L(x) is a function derived from a statistical nature, U(x) is a function defined based on the prior information on an object for radiography (definite theoretical nature which a reconstruction image x is likely to possess). U(x) is generally called "penalty function". An example of iterative formula using the penalty function is shown below (see the following equation (6)).

[Math 6]

$$x_j^{(k+1)} = x_j^{(k)} - \frac{x_j^{(k)}}{\sum_{i=1}^{I} w_i a_{ij} + x_j^{(k)} c_j^{(k)}} \left( \frac{\partial L(x^{(k)})}{\partial x_j} + \frac{\partial U(x^{(k)})}{\partial x_j} \right) \quad (6)$$

where $c^{(k)}_j$ is a j-th pixel value of an approximate curvature image of regularization function U(x) adjacent k-th estimated solution $x^{(k)}$.

(9) In each foregoing embodiment, the error distribution of the element data (i-th measurement data points) constituting the measurement data set (measurement data) has been Poisson distribution, but Poisson distribution is not limitative. Gaussian distribution may be used. The error distribution, when it is Gaussian distribution, is used with an X-ray computerized tomographic apparatus (X-ray CT apparatus).

INDUSTRIAL UTILITY

As described above, this invention is suitable for an image reconstruction technique covering the whole field of body section image radiographic apparatus with radiation detecting apparatus, such as positron emission tomographic apparatus (PET apparatus), single photon emission tomographic apparatus (SPECT apparatus), X-ray computerized tomographic apparatus (X-ray CT apparatus) and so on.

REFERENCE SIGNS LIST

1 . . . partial ring type PET apparatus
2A, 2B . . . detector units
3 . . . gamma-ray detectors
L(x) . . . weighted likelihood function
$w_i$ . . . weight coefficient (likelihood weight coefficient)
SA . . . streak artifacts
h, g . . . discrete variables
U(x) . . . penalty function
M . . . subject

The invention claimed is:

1. An image reconstruction processing method for performing an image reconstruction process to reconstruct as a multidimensional digital image, from a measurement data set of a subject obtained by a radiation detecting apparatus, a physical quantity distribution of the subject relating to an occurrence factor of the measurement data set, wherein:

a first multivariate function in which the digital image is regarded as unknown is
(1) a data function expressed by a sum of partial functions composed based on an error distribution of element data constituting the measurement data set; or
(2) a sum of the data function expressed by the sum of the partial functions composed based on the error distribution of the element data constituting the measurement data set, and a second multivariate function composed based on prior information on the physical quantity distribution;
the image reconstruction processing method weights the partial functions with a weight coefficient of back projection for a reconstruction image of the element data corresponding to the partial functions, and executes reconstruction processing steps based on optimization calculations of the first multivariate function consisting of a weighted data function or the sum of the weighted data function and the second multivariate function composed based on prior information on the physical quantity distribution;
the radiation detecting apparatus is one of a positron emission tomographic apparatus, a single photon emission tomographic apparatus, and an X-ray computerized tomographic apparatus;
the weight coefficient is set by a computer based on directionality of linear noises occurring in the image reconstructed with a constant weight coefficient independent of the element data; and
the weight coefficient for the element data along a running direction of the linear noises is smaller than the weight coefficient for the element data not along the running direction of the linear noises.

2. The image reconstruction processing method according to claim 1, wherein:
the radiation detecting apparatus is one of the positron emission tomographic apparatus and the single photon emission tomographic apparatus; and
the measurement data set is one of sinogram data, histogram data, and list mode data.

3. The image reconstruction processing method according to claim 1, wherein the error distribution is one of Poisson distribution and Gaussian distribution.

4. An image reconstruction processing method for performing an image reconstruction process to reconstruct as a multidimensional digital image, from a measurement data set of a subject obtained by a radiation detecting apparatus, a physical quantity distribution of the subject relating to an occurrence factor of the measurement data set, wherein:

a first multivariate function in which the digital image is regarded as unknown is
(1) a data function expressed by a sum of partial functions composed based on an error distribution of element data constituting the measurement data set; or
(2) a sum of the data function expressed by the sum of the partial functions composed based on the error distribution of the element data constituting the measurement data set, and a second multivariate function composed based on prior information on the physical quantity distribution;
the image reconstruction processing method weights the partial functions with a weight coefficient of back projection for a reconstruction image of the element data corresponding to the partial functions, and executes reconstruction processing steps based on optimization calculations of the first multivariate function consisting of a weighted data function or the sum of the weighted data function and the second multivariate function composed based on prior information on the physical quantity distribution, the weight coefficient being set by a computer;

the radiation detecting apparatus is one of a positron emission tomographic apparatus, a single photon emission tomographic apparatus, and an X-ray computerized tomographic apparatus;

the radiation detecting apparatus includes radiation detectors formed into a plurality of detector units separated from each other; and the weight coefficient for the element data along straight line directions connecting between detector elements in a same detector unit is smaller than the weight coefficient for the element data along straight line directions connecting between detector elements in mutually different detector units.

5. The image reconstruction processing method according to claim 4, wherein:

the radiation detecting apparatus is one of the positron emission tomographic apparatus and the single photon emission tomographic apparatus; and the measurement data set is one of sinogram data, histogram data, and list mode data.

6. The image reconstruction processing method according to claim 4, wherein the error distribution is one of Poisson distribution and Gaussian distribution.

7. An image reconstruction processing method for performing an image reconstruction process to reconstruct as a multidimensional digital image, from a measurement data set of a subject obtained by a radiation detecting apparatus, a physical quantity distribution of the subject relating to an occurrence factor of the measurement data set, wherein:

a first multivariate function in which the digital image is regarded as unknown is
(1) a data function expressed by a sum of partial functions composed based on an error distribution of element data constituting the measurement data set; or
(2) a sum of the data function expressed by the sum of the partial functions composed based on the error distribution of the element data constituting the measurement data set, and a second multivariate function composed based on prior information on the physical quantity distribution;

the image reconstruction processing method weights the partial functions with a weight coefficient of back projection for a reconstruction image of the element data corresponding to the partial functions, and executes reconstruction processing steps based on optimization calculations of the first multivariate function consisting of a weighted data function or the sum of the weighted data function and the second multivariate function composed based on prior information on the physical quantity distribution, the weight coefficient being set by a computer;

the radiation detecting apparatus is one of a positron emission tomographic apparatus, a single photon emission tomographic apparatus, and an X-ray computerized tomographic apparatus;

the radiation detecting apparatus includes radiation detectors constructed to measure detection depth position information on radiation;

the weight coefficient is dependent on the detection depth position information corresponding to the measurement data set;

when N is a natural number larger than or equal to 2, the radiation detectors are constructed to measure detection depth position information of N stages; and when, in detector elements constituting the radiation detectors, stage numbers of detection depth of two detector elements having measured a coincidence is set to g and h ($1 \leq g$, $h \leq N$), respectively, so that the numbers become larger from shallow stage to deep stage, the weight coefficient is a two-dimensional function having the stage numbers g and h as discrete variables, the two-dimensional function being such that a one-dimensional function for the other variable obtained when one variable is fixed is a nonincreasing function.

8. The image reconstruction processing method according to claim 7, wherein:

the radiation detecting apparatus is one of the positron emission tomographic apparatus and the single photon emission tomographic apparatus; and the measurement data set is one of sinogram data, histogram data, and list mode data.

9. The image reconstruction processing method according to claim 7, wherein the error distribution is one of Poisson distribution and Gaussian distribution.

* * * * *